United States Patent [19]

Hounsfield

[11] 4,206,359

[45] Jun. 3, 1980

[54] RADIOGRAPHY

[75] Inventor: Godfrey N. Hounsfield, Newark, England

[73] Assignee: E M I Limited, Hayes, England

[21] Appl. No.: 544,799

[22] Filed: Jan. 28, 1975

Related U.S. Application Data

[63] Continuation-in-part of Ser. No. 489,084, Jul. 17, 1974, Pat. No. 3,934,142.

[30] Foreign Application Priority Data

Jan. 31, 1974 [GB]  United Kingdom ................. 4562/74

[51] Int. Cl.² ........................................... G01N 21/34
[52] U.S. Cl. ................................................ 250/445 T
[58] Field of Search ........... 250/362, 363, 336, 445 T, 250/366, 395, 369

[56] References Cited

U.S. PATENT DOCUMENTS

| | | | |
|---|---|---|---|
| 3,778,614 | 12/1973 | Hounsfield | 250/362 |
| 3,780,290 | 12/1973 | Hoffer | 250/363 S |
| 3,784,820 | 1/1974 | Miraldi | 250/362 |
| 3,808,440 | 4/1974 | Petit-Clerc | 250/363 S |
| 3,852,611 | 12/1974 | Cesar | 250/445 T |
| 3,924,129 | 12/1975 | LeMay | 250/369 |

OTHER PUBLICATIONS

Ramachandran & Lakshminarayanan, "Reconstruction by Convolution," Procedures National Acadamy of Science, vol. 68, No. 9, pp. 2236-2240, Sep. 1971.

*Primary Examiner*—David C. Nelms
*Attorney, Agent, or Firm*—Cooper, Dunham, Clark, Griffin & Moran

[57] ABSTRACT

In a method of examining a body by means of penetrating radiation a source is arranged to provide a fan shaped spread of the radiation and a detector examines the intensity of a plurality of individual beams of radiation defined from the fan. The source and detector are orbited about the body so that the beams are provided at a plurality of angles relative to the body. In the associated processing, the data signals from the detectors are combined so that each combined signal relates to two beams 180° to each other in the orbital movement. A further selection is also made of the data signals so that they are provided to a further processing stage in sets for which each set is of data signals relating to beams which are substantially parallel to each other.

18 Claims, 7 Drawing Figures

| 15° | 0° | -15° |
|---|---|---|
| 30° | 15° | 0° |
| 45 | 30° | 15° |
| 60° | 45° | 30° |
| ⋮ | ⋮ | ⋮ |
| 165 | 150° | 135° |
| ±180° | 165° | 150° |
| -165° | ±180° | 165° |
| -150° | -165° | ±180° |
| -135° | -150° | -165° |
| ⋮ | ⋮ | ⋮ |
| -30° | -45° | -60° |
| -15° | -30° | -15° |
| 0° | -15° | -30° |

RADIOGRAPHY

This application is a continuation-in-part of applicant's copending application Ser. No. 489,084, filed July 17, 1974, for an improvement in "Radiography", which application has become U.S. Pat. No. 3,934,142.

This invention relates to a method of and apparatus for examining a body by means of radiation such as X or Y radiation.

The method and apparatus according to the invention can be used to assist in the production of radiographs in any convenient form, such as a picture on a cathode ray tube or other image forming device, a photograph of such a picture, or a map of absorption coefficients such as may be produced by a digital computer and on which contours may subsequently be drawn.

In the method of, and apparatus, for examining a body described in U.S. Pat. No. 3,778,614, radiation is directed through part of the body, from an external source, in the form of a pencil beam. A scanning movement is imposed on the beam so that it takes up in turn a large number of differing dispositions, and a detector is used to provide a measure of the absorption of the beam in each such disposition after the beam has passed through the body. So that the beam takes up these various dispositions the source and the detector are reciprocated in a plane and are orbited about an axis normal to the plane. The various dispositions thus lie in a plane through the body over which the distribution of absorption coefficient for the radiation used is derived by processing the beam absorption data provided by the detector. The processing is such that the finally displayed distribution of absorption is the result of successive approximations.

The method and apparatus described in the aforesaid U.S. patent has proved to be successful for producing cross-sectional representation of parts of the living body, such as the head.

The arrangement described in the aforesaid specification for calling out the scanning operation however relatively slow and for scanning some parts of the body a much faster scanning rate is desirable. Apparatus capable of achieving a faster scanning rate is described in U.S. Ser. No. 532,188 filed Dec. 12, 1974 (Hounsfield et al) and according to this application the derivation of the absorption data signals is achieved by directing a fan-shaped spread of X-rays through the body and providing a bank of detectors at the other side of the body to measure the radiation transmitted along a set of beam paths within the fan. The fan shaped spread subtends an angle sufficient to include the whole region of interest in the plane of the body, so that a complete scan can be effected merely by orbiting the source and the detectors about the body.

In U.S. Pat. No. 3,924,129, there is described an apparatus for processing the absorption data by a convolution method. This latter method allows relatively faster processing than the iterative method of the said U.S. Pat. No. 3,778,614.

According to one aspect of the invention there is provided an apparatus for examining a body by means of penetrating radiation such as X- or γ- radiation, including source means for irradiating the body with a fan shaped spread of radiation, detector means comprising a plurality of detectors for detecting the radiation after passage through the body, each respective detector receiving radiation along a narrow but divergent beam path, means for scanning the source and detector means around the body so as to irradiate a planar section of the body along beams of said radiation at a plurality of angular positions in the plane of said section, so that a reconstruction of the distribution of absorption of the radiation in said section can be produced in response to beam data signals derived from the detectors, wherein absorption data signals representing the absorption of radiation along paths of substantially uniform width are produced by combining output signals relating to beam paths at angular positions substantially 180° apart.

According to another aspect of the invention there is provided a method of examining a body including the steps of irradiating the body with a fan shaped spread of penetrating radiation, such as X- or γ- radiation, scanning the source of the radiation and a detector means comprising a plurality of detectors sensitive to the radiation, around the body so as to irradiate a planar section of the body along beams of radiation at a plurality of angular positions in the plane of the section, combining beam data signals provided by said detector means related to beams of radiation at angular positions 180° apart to derive further data signals related to radiation along beam paths of substantially uniform width so that said further data signals can be processed to derive a reconstruction of the distribution of absorption of the radiation in the said section.

According to a further aspect of the invention there is provided an apparatus for examining a body by means of penetrating radiation such as X- or γ- radiation including source means arranged to irradiate a planar section of the body by means of a fan shaped spread of radiation in the plane of said section, detector means comprising a plurality of detectors arranged to determine the absorption suffered by said radiation after passage through the body along a plurality of angularly distributed beam paths in said fan, means for scanning the source and detector means around the body so as to irradiate the said section from a plurality of directions so that from the absorption beam data signals provided by said detectors, a reconstruction of the distribution of absorption of the radiation in said slice can be produced, wherein means are provided for selecting signals from said detectors, related to corresponding positions of said detectors in the scanning motion, to produce sequences of signals relating simply to parallel sets of beams of radiation.

In order that the invention may be clearly understood and readily carried into effect, the same will now be described with reference to the accompanying drawings in which.

Figure 1:
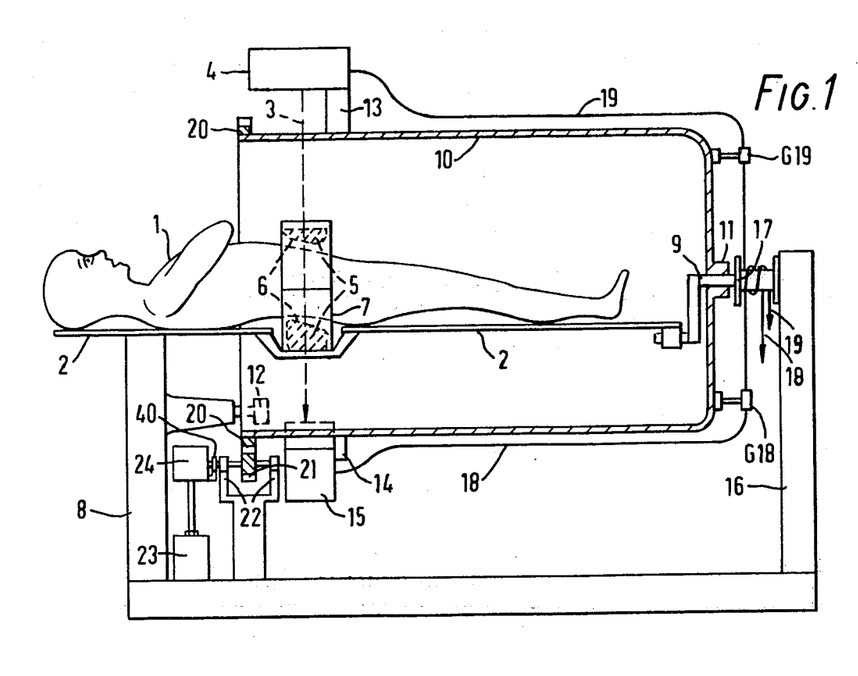
FIG. 1 shows the general layout in side elevation of an apparatus in accordance with the invention.

In FIG. 1 a patient 1 is shown lying on supporting means and his body is subject to examination by X radiation indicated in broken line at 3. This radiation is generated by a source 4 and forms a fan shaped spread in a plane lying at right angles to the plane of the figure. It will be appreciated that the patient supporting means has to be sufficiently long to allow any desired section of the patients body to be located in the plane of the X-radiation.

In the region of the exploring radiation, the body of the patient is surrounded by a suitable medium, which in this case is water, having an absorption coefficient for the radiation closely similar to that of body tissue. The water is shown in the figure at 5 and is contained within an envelope, or bag 6. The envelope 6 is positioned within a ring like structure 7 which may be of metal such as duralumin.

The ring member 7 is in two parts as described in U.S. Ser. No. 532,188 filed Dec. 12, 1974 (Hounsfield et al) and is in this example fixed to the supporting means 2. It should be noted that ring 7 may be mounted in movable relation to supporting means 2 if desired, to facilitate entry of the patient and further that supporting means 2 may be arranged to be movable in relation to other parts of the apparatus for the same purpose and for correct positioning in relation to the X-ray beam.

Supporting means 2 is positioned at one end by a support 8 and at the other end by a fixing bracket 9. Bracket 9 is in the form of an axle member which has an axis about which the orbiting motion of the X-ray source 4 takes place, as will be made more clear.

Around the body of the patient when he is located in position in the apparatus there is disposed a surround or frame 10 which is cylindrical along its length having a longitudinal axis which is the axis of the bracket 9. At this end adjacent to this latter bracket it is closed and supported by a bearing 11 which, in turn, is supported by the axle of bracket 9. At its other end it is open to allow of positioning the patient within it, and at this end it is supported on rollers 12 which have suitable fixed bearings. These rollers are such that the surround member 10 is free to rotate on its axis, which as has been indicated is the axis about which the orbiting motion of the X-ray source 4 takes place. The source 4 is mounted on the surround member 10 by means of a support 13. Directly opposite the source 4 there is mounted on the surround member 10, by means of a support 14, a detector means 15 so as to provide radiation absorption data from the body of the patient in the plane of the radiation from the source 4.

The axle of bracket 9 is carried by a support 16 and adjacent to that support and surrounding the axle is a bobbin 17. This last element is fixed to the support 16 and wound round it are cables 18 carrying absorption data from the detector means 15 to the processing unit and cables and connections 19 supplying power, control signals and cooling fluid to the X-ray source 4. With the orbiting motion of the source and detector means the cables wind on or off the bobbin 17 correspondingly. They are fed to the bobbin via guides G18 and G19 which are mounted on member 10. At the bobbin the cables and other connections are secured and thense pass to their respective connecting units, including the data processing unit mentioned, and a power supply unit.

For the purpose of achieving the orbiting motion the rim of surround member 10 at its open end is provided with gear teeth 20. Engaging with these teeth is a gear wheel 21, mounted on a shaft supported as shown by bearings 22. Gear wheel 21 is driven by a reversible motor 23 via a gearbox 24. It will be appreciated that gear teeth 20 may be provided at any desired position on member 10. A scanning timing signal unit 40 provides signals indicating the progress of the rotation of source 4. This may be a graticule on the shaft of gear 21 cooperating with a light source and photocell or alternatively a suitable cam arrangement.

Figure 2:
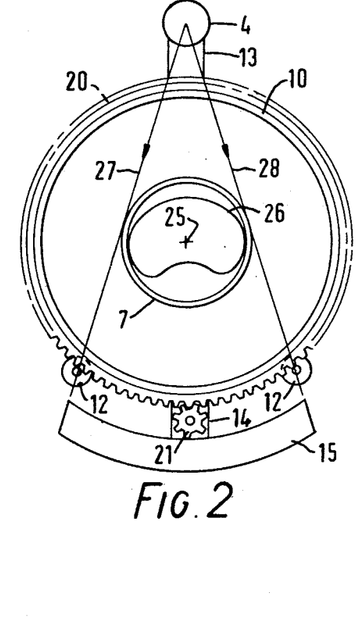
FIG. 2 illustrates the same apparatus in end elevation.

FIG. 2 as stated shows an end view of the apparatus illustrated in FIG. 1 and reference numerals have the same significance as in relation to FIG. 1. At 25 in FIG. 2 there is indicated the location of the orbital axis and 26 shows the outline of the cross-section of the patient's body in the plane of the exploring radiation.

FIG. 2 furthermore shows rays 27 and 28 indicating the extremes of the fan of radiation from source 4. It will be seen that the detector means 15 extends over the whole spread of the fan of radiation between rays 27 and 28. As explained in U.S. application Ser. No. 493,403 (LeMay) means may be provided to examine a desired region of the patients body in greater detail but no provision is made for that in the present example. In addition further details of the ring member 7 and associated retaining means are described in the said U.S. application Ser. No. 532,188 filed Dec. 12, 1974 (Hounsfield et al).

Figure 3:
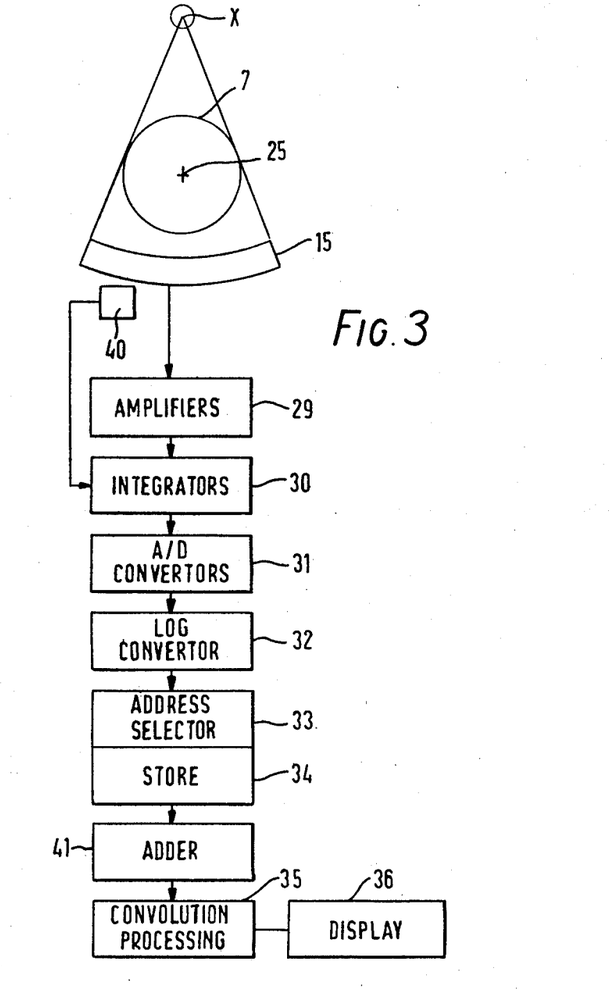
FIG. 3 shows in diagrammatic form the general layout of those parts of the apparatus concerned with processing of the absorption data.

FIG. 3 sets out diagrammatically the general arrangement of the processing for the apparatus shown in FIGS. 1 and 2.

In this figure the point X denotes the point of emission of X-radiation from the source 4, the point 25 the location of the orbital axis, 7 the location of the ring member and 15 the detector means providing absorption data for processing.

Detector means 15 includes a plurality of detectors and corresponding collimators defining individual beams of radiation as described in the aforesaid copending applications. In the course of the orbital movement of the apparatus the absorption data are obtained as output currents from the photomultipliers associated with the detectors. The data are amplified by respective amplifiers 29. The gains of the amplifiers are individually adjusted to compensate for the differing sensitivities of the various scintillation crystals of the detectors. If desired the gains of the amplifiers may be commonly controlled to compensate for any variations that may occur in the emission intensity of X-ray source 4. The currents as amplified are respectively integrated by Miller integrator circuits 30. The integrators are arranged, in response to timing signal unit 40 to operate for such a period that each individual beam corresponding to a detector extends over an angle of substantially 2/15 degrees, in this example, due to the orbital motions. Corresponding to this, the detectors are arranged at such a spacing that the centrelines of those beams are at substantially 2/15 degrees spacing, each being centred on point source X. The outputs of the integrators are converted from analogue to digital forms by converters 31.

It is desired that the final image reconstruction shall represent the distribution of the absorption coefficient over the area of the cross section under examination, the absorption coefficient being the absorption per unit length, in the immediate vicinity of a given point, of an exploring beam passing the point. To achieve the desired result it is necessary that each output signal derived from the detector means 15 shall be converted to its logarithmic form. For this purpose log converter 32 operates on the digital data from A/D converters 31. Log converter 32 comprises logarithmic look-up tables according to known usage. The data is written into a store 34 in response to an address selector 33, in a manner to be further described, and from there it is subject to convolution processing and interpolation in unit 35 before being displayed in a display and control unit 36. The operation and nature of processing unit 35 has been fully described in U.S. Pat. No. 3,924,129.

The technique described therein can be described as producing a corrected layergram and requires the data to be provided in sets each relating to a set of substantially parallel beams of radiation, the data of each set being provided term by term. Consequently address selector 33 and store 34, which can form part of a suitably programmed digital computer, are programmed to arrange the data into such "parallel" sets.

In the apparatus being described the integrators 30 operate for such a time that, considering the orbital motion during the integration period, the effective spread of the beam path is 2/15°, so that output signals are obtained after each 2/15° movement. Furthermore the spacing of beams in the fan is arranged so that the centrelines of adjacent beams are at substantially 2/15° spacing. Thus after each increment of rotation of this magnitude each beam will assume a position which is parallel to the position which one of its neighbours occupied prior to this increment of rotation. It is therefore possible by suitable selection of data from store 34 to produce signals corresponding to sets of parallel beams at 2/15° separation.

Figure 4A:
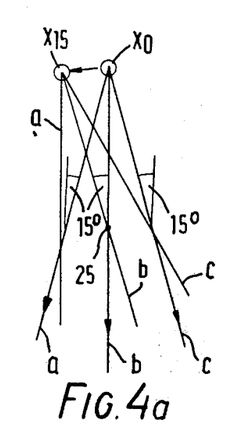
FIGS. 4a and 4b are diagrams used for explaining the invention.

This is illustrated in FIG. 4 which shows a fan of three beams with centrelines at 15° spacing. The beams represent the centre and extreme beams of a 30° fan of beams but for the moment may be considered as if they are the only beams of a three beam fan. The three beams, designated a, b and c are illustrated in FIG. 4a, the corresponding detectors not being shown, for a position of the point source Xo for which centre beam b makes an angle 0° with an arbitrary zero line vertical in the figure, and the other beam centrelines make the angles shown. It will be seen that when the source is orbited 15° to position $X_{15}$, corresponding to the beam centreline spacing, beam a takes up a position parallel to the previous position of beam b similarly b becomes parallel to c. Beam c takes up a new inclination. A further 15° movement will take beam a parallel to the original position of beam c etc. and thus sets of parallel beam positions are being built up.

Considering this it can be seen that if the data from converters 32 are directed into store 34 to locations labelled with an angular position for the corresponding beam, they can be extracted as sets of data for each such angle.

Figure 4B:
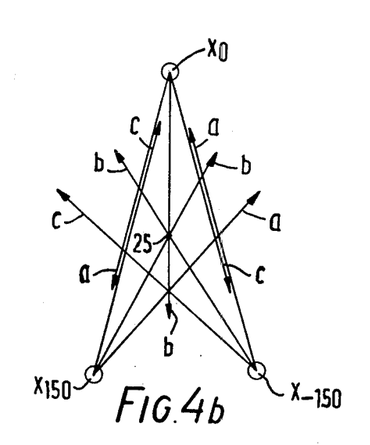
Figure 5:
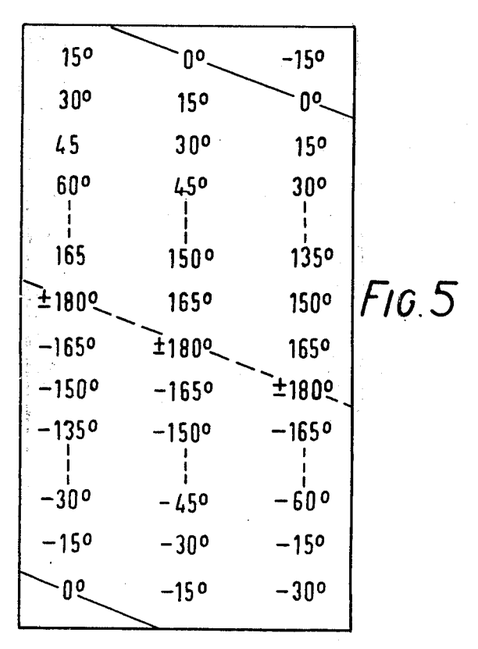
FIG. 5 illustrates the arrangement of the absorption data in a preprocessing store and FIG. 6 illustrates a special circuit for arranging the absorption data in a form suitable in particular to the convolution processing.

This is shown, for the illustrative set of three beams, in FIG. 5. The figure corresponds to a matrix of locations in store 34 with each such location being identified by the angle, relative to the arbitrary zero, of that beam for which the datum in the location was derived. Each detector provides data to elements of a column labelled a, b or c in correspondence with FIG. 4. As the centre beam (b) rotates through 360° all of the beams rotate through a series of angles including those shown. The 360° position, which is the same as 0°, is not shown. It will be understood also that −180° is the same as +180° and accordingly positive angles greater than 180° have been shown on the corresponding negative angles. The data are entered into the store in rows, each row corresponding to the mean angular position for one reading from each detector, as they are derived. For clarity not all rows have been shown. It can be seen that diagonal set of locations provide data for beams which are at the same angle and therefore parallel. It should be noted that although beams at the same angle are parallel they are not identical. The 0° set of beams, indicated by the solid diagonal line, forms a complete parallel set although the data must be obtained from the first rows and the last row. That set will, therefore, not be complete until all data has been derived. The data from the locations for such parallel sets are selected from store 34 and transferred serially to processor 35 for the convolution processing described in U.S. Pat. No. 3,924,129. The data may be transferred to processor 35 after all data has been derived and stored or, if desired, each "parallel" data set may be transferred as soon as it is completed. In the illustrative example of FIG. 5 the 15° set is the first to be completed.

In the present practical example of the apparatus illustrated in FIGS. 1 to 3 the store 34 has, of course, many more locations than that shown in FIG. 5. There are rows for each of the 2/15° orbital positions and a column for each of the detectors of detector means 15.

In regard to the arrangement of beams considered in U.S. Pat. No. 3,924,129 and application Ser. No. 493,403 it is to be noted that the beams are in those cases implicity treated as though they are of uniform width. However, in the apparatus of FIGS. 1 and 2, the beams defined by the detectors are not of this character, being narrower on the point X-ray source side of the explored field and wider on the detector side. The effect of this disparity is minimised in the apparatus described by not restricting the orbital motion to the 180° which would be in theory sufficient, but by continuing it for 360° so that for every beam disposition of the first 180° of scan there is a second which is identical except for the fact that the direction of passage of the radiation is reversed, and with it the sense of the disparity. The average of the two beam absorptions is then taken to produce data corresponding to a beam path of substantially uniform width considering the limited angular spread of each beam.

The use of two beams at 180° spacing to irradiate one beam path has the further advantage that the "skin dose" of radiation, resulting from the required total X-ray intensity for that path, is divided equally between surfaces at opposite ends of the path instead of being substantially concentrated at one end.

However it should be understood that data for each beam should be combined only with that for a beam at substantially 180° relation of scan. For a fan of beams, such as that of FIGS. 4 and 5, only data for the centre beam (b) can be combined with data for the same beam inverted so that data for the 180° set (broken diagonal line) is combined with that for the 0° set.

The position for the other beams of the set is shown in FIG. 4b. Three positions of the point source X are shown, identified by subscripts which represent the corresponding angular position of centre beam b. It will be seen that, for $X_{150}$, beam c shares a beam path with beam a of Xo and these may therefore be combined to give a uniform width beam. Similarly c at Xo shares a path with a at $X_{150}$. Considering this in relation to the storage location of FIG. 5 it can be seen that the 180° beam set data can be combined with the 0° data, provided the two sets are withdrawn from storage in inverse order. The combinations will thus be: $(a_o + c_{180})$, $(b_o + b_{180})$ and $(c_o + a_{180})$.

For this purpose the digital computer forming address selector 33 and store 34 in FIG. 3 is arranged to derive the data from the locations in the manner described, combine them and transfer them to processor 35. For the purpose of this combination an adder 41 is provided between store 34 and processing unit 35. This may also be included in the digital computer. Address selector 33 provides the data for the two sets in pairs to be combined. Adder 41 is provided with a storage location for one beam data signal to retain the first of each pair and then adds the second to the first before passing the new combined data on to processor 35. It will be understood that other means of combining the data may be employed. For instance an individual reconstruction of absorption coefficients may be derived for each pair of "opposite" parallel sets (e.g. 180° and 0°) and the two pictures combined on display or otherwise. The term "combination of the data" is intended to include all such combination.

As described in U.S. Pat. No. 3,924,129 unit 35 shown in FIG. 3 may be provided as a suitable programmed digital computer. In a practical example of the invention the functions of units 33, 34, 41 and 35 may all be provided by a single digital computer. However they have been shown in FIG. 3 as separate units in order that their functions may be more clearly distinguished.

Figure 6:
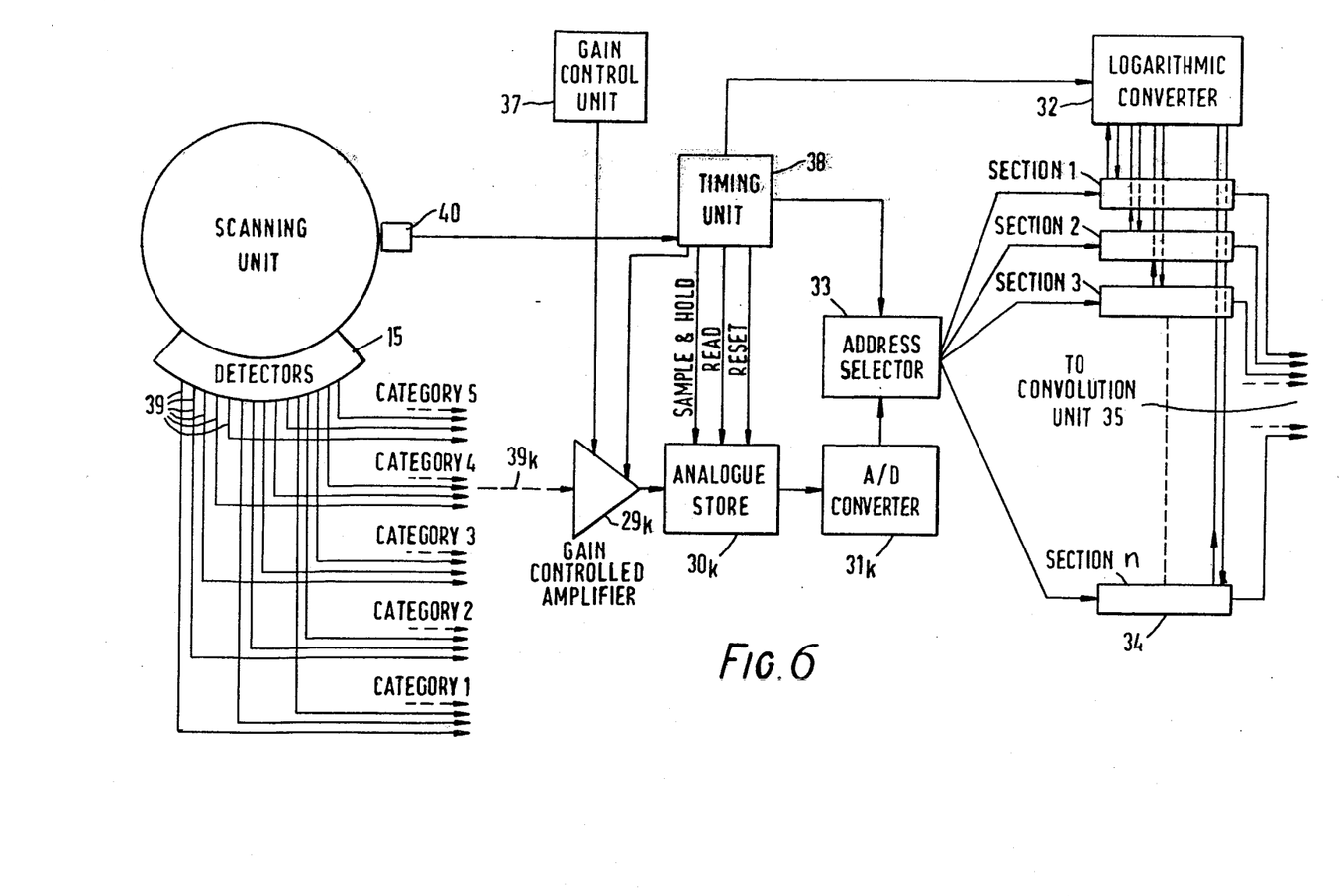

Instead of using a general purpose digital computer to perform the function of sorting the data into "parallel" sets, a special purpose computer may be employed. An example of such an arrangement is shown in FIG. 6.

Disregarding for the moment the plurality of conductors 39, divided into five categories, conductor $39_k$ transmitting output signals from a detector k will be considered to be typical of all conductors from such detectors.

As mentioned hereinbefore, the duration of sampling of the output of each detector such as k is such that the effective beam width, resulting from the orbital movement is that desired. In practice an "aperture effect" will cause the beam width to be greater than this so that some overlap is provided as described, for example, in U.S. patent application Ser. No. 471,658 (Hounsfield). The output is amplified by amplifier $29_k$ controlled by gain control unit 37. Analogue store $30_k$ is the Miller integrator referred to hereinbefore operating in its known role of an analogue store used to sample and hold, thereafter to be reset to be available for further sampling in the same manner. A/D converter $31_k$ also operates as in FIG. 3. In response to address selector 33 the data are distributed to store 34 which in this case is divided into sections 1, 2, 3 . . . n. All the data from conductors such as k are also distributed to these sections of store 34. However in this example each section of store 34 holds the data of one "parallel" set corresponding to a diagonal of FIG. 5. Thus this circuit is unlike that of FIG. 3 which accepts data as desired and perform the sorting into parallel sets as a timing disassociated from that of the scanning. The FIG. 6 circuit requires data to be distributed to sections of store 34 and hence into "parallel" sets as they are derived and therefore the timing must be coordinated with the scanning. For this purpose address selector 33 is controlled by timing unit 38 which receives input signals from scanning timing signal unit 40. Timing unit 38 is also used to control the integrators 30.

For the purpose of combining data for beams at 180° relation of scan it should be noted that although data for the first 180° of scan are applied to the sections of store 34 in one order those for the second 180° (i.e. of the parallel sets, not of the scanning position) are applied in the reverse order to effect the combination described with respect to FIG. 4b. For this purpose address selector 33 is suitably programmed. When any section of store 34 has received all the data for its parallel set that data is transferred serially to convolution unit 35 for processing as referred to hereinbefore.

Log converter 32 could be provided between converter 31 and selector 33 in this example as in FIG. 3. However it has been shown cooperating with store 34 to withdraw data from respective storage locations, convert to logarithmic form and replace them in the same storage locations. In this manner it is possible to provide a log converter to operate on one signal at a time instead of on several simultaneously as in FIG. 3. For the purpose described log converter 32 is controlled by timing control 38.

Considering the outputs from detector means 15 in FIG. 6 it will be seen that they are grouped into five categories. This feature, which is optional, enables the number of integrators to be reduced by one fifth although each channel should still have its own amplifier. In this arrangement the detectors are divided so that the first, sixth, eleventh etc. are allocated to category one, the second, seventh etc. to category two, the third etc. to category three, the fourth etc. to category four and the fifth etc. to category five. Thus the detectors of the five categories are interlaced. The data is derived from these detectors in conjunction with 2/15° orbital movements as follows. During the first 2/15° all detectors of category one are sampled. During the next 2/15° all detectors of category two are sampled for beam paths parallel to those used by the category one detectors. In the next 2/15° the detectors of category three are sampled and so on. In the sixth 2/15° the detectors of category one are sampled again for beam paths $\frac{2}{3}$° displaced from those previously used for all five categories. Thus data for $\frac{2}{3}$° spaced parallel sets are derived but with five times the number of beam paths otherwise possible for the number of integrators provided. For this purpose each integrator takes one corresponding beam from each category (e.g. all fifth position beams). Each amplifier is gated by timing unit 38 to provide data to the integrator only as required. The gating may be provided otherwise if required, for example the detector photomultipliers may be so gated or independent gates or switches provided.

It will be understood that the features of the present invention may be utilised with any signal processing such as that described in U.S. Pat. No. 3,778,614. Furthermore the invention may be utilised with scanning arrangements other than that described hereinbefore. For example the rotation need not be the simple rotation described but may be a more complex movement if desired for other purposes. In relation to the scanning arrangements described the examples of beam widths and spacings which have been given may be varied as desired provided the correct relationships are maintained. Furthermore each beam may be examined by more than one detector if desired.

In the example described above, the invention is used in a medical radiology machine of the type sometimes referred to as CAT scanners, in which radiation travels along a substantially planar slice through the patient. The X-radiation source orbits around the patient so as to send radiation along a number of directions which are at different angles to each other in the slice. The intensity of the radiation emerging from the slice is measured along each of a number of pencil-thin beam paths such that any point in the slice is traversed by a great number of such beam paths. The resulting measurements are processed, for example as described in U.S. Pat. Nos. 3,778,614 and 3,924,129, to generate a picture in which each point has a brightness corresponding to the X-radiation response characteristics of the correspondingly positioned point in the slice. The picture is similar to what would be seen if the patient were cut in two along the slice and one looked at the resulting cross section through the body.

In using convolution processing of the type described in U.S. Pat. No. 3,924,129, it is desirable to process measurement signals for beam paths which are in sets where each set consists of a reasonably uniform distribution of parallel beam paths. However, the measurements derived from a scanning motion in which the radiation source orbits around the body, without substantial lateral scanning, are not derived in such sets of parallel beam paths, and one aspect of this invention is to provide a technique for selecting from the measurement signals sets of signals corresponding to sets of parallel beam paths. As described in detail above, this selecting may take place at the time the measurement signals are derived from the detectors or at the time the measurement signals, which have been derived and stored, are read out from storage for use in processing. The various sets of parallel beam paths are disposed at respective angles within the irradiated slice and are preferably distributed evenly over approximately 180°.

While a useful picture may be derived from orbiting the source of radiation over only half a revolution, another aspect of this invention is directed to orbiting the source over more than that, for example a full revolution, and combining the measurements for beam paths that are along the same line but at opposite directions. One advantage of this is that the radiation dosage to the patient is distributed more uniformly and another advantage is that the combined measurement corresponds to a beam path of more uniform cross section.

What I claim is:

1. An apparatus for examining a body by means of penetrating radiation such as X- or γ- radiation including source means arranged to irradiate a planar section of the body by means of a fan shaped spread of radiation in the plane of said section, detector means comprising a plurality of detectors arranged to determine the absorption suffered by said radiation after passage through the body along a plurality of angularly distributed beam paths in said fan, means for scanning the source and detector means around the body so as to irradiate the said section from a plurality of directions so that from the absorption beam data signal provided by said detectors, a reconstruction of the distribution of absorption of the radiation in said slice can be produced, wherein means are provided for selecting signals from said detectors, related to corresponding positions of said detectors in the scanning motion, to produce sequences of signals relating to sets of parallel beams of radiation.

2. An apparatus according to claim 1 wherein said scanning means is arranged to orbit the source and detector means about a common axis normal to the plane of said slice and wherein said beam data signals are derived from detectors corresponding to beam paths at a predetermined angular spacing in said fan in sequence at time intervals such that the orbital motion in each of those time intervals is approximately equal to the said angular spacing.

3. Apparatus according to claim 1 wherein said scanning means is arranged to scan said source and said detector means through an angle exceeding 180° sufficient for the production of sequences of signals relating to parallel sets of beams of radiation which are symmetrical about the axis of the scanning, and which are angularly distributed at least over 180°, and means are provided for subjecting said sequences of signals to convolution processing and interpolation to produce a representation of the distribution of absorption in relation to said slice.

4. Medical radiographic apparatus for examining a substantially planar section of the body of a patient by means of penetrating radiation, such as X-radiation, including source means arranged to irradiate said section of the body by means of a fan-shaped spread of radiation diverging from said source, means for positioning the body in relation to said source, a support on which said source is mounted and adapted for angular movement, a plurality of detectors adapted to receive radiation after passage through said body, the detectors receiving radiation along relatively narrow beam paths angularly distributed across said fan, circuits coupled to said detectors providing data signals each related to radiation transmitted through said body and received by the detector along a respective beam path, said circuits providing data signals respective to each of a plurality of said paths at each of a plurality of angular positions of said source about said axis, a selector for selecting from among said data signals different sequences of signals, each sequence of signals relating to radiation transmitted through said body along a set of parallel beam paths, and the different sequences of signals corresponding to sets of beam paths angularly distributed about said axis, and means for deriving a representation of a variable characteristic, with respect to said radiation, of said section of the body.

5. Apparatus according to claim 4, wherein said means for producing relative angular movement is arranged to move said source through an angle exceeding 180° sufficient for the production of sequences of signals relating to parallel sets which are symmetrical about said axis and are angularly distributed about at least 180° and means are provided for subjecting said sequences of signals to convolution processing and interpolation to produce a representation of the distribution of absorption in relation to said section.

6. Medical radiographic apparatus comprising
means defining a patient position and means for generating a fan of radiation which diverges in moving away from the source means in a substantially planar region intersecting the patient position;
means for substantially continuously orbiting the fan of radiation within said region around an axis located within the patient position;
means for detecting the radiation emerging from the patient position in said plane along a plurality of radiation beam paths which are within said fan of radiation and are at an angle to each other in said plane to obtain a corresponding measurement signal for each of said beam paths;
means for selecting, from said measurement signals, sets of signals which correspond to sets of beam paths wherein the beam paths within each set are substantially parallel to each other; and
means for processing said sets of measurement signals to derive a representation of the distribution in said region of a characteristic related to the response to said radiation of the matter traversed thereby.

7. Medical radiographic apparatus for examining a slice of the body of a patient by means of penetrating radiation, such as X-radiation, including source means arranged to irradiate said slice of the body by means of a fan-shaped spread of radiation diverging from said source, means for positioning the body in relation to said source, a support, adapted for angular movement, and on which said source is mounted, a plurality of detectors adapted to receive radiation after passage through said body, the detectors receiving radiation along relatively narrow beam paths angularly distributed across said fan, circuits coupled to said detectors providing data signals each related to radiation transmitted through said body and received by the detector along a respective beam path, means for angularly moving said support and with it said source about an axis intersecting said slice so that said circuits provide data signals respective to each of a plurality of said paths at each of a plurality of angular positions of said source about said axis, said means for angularly moving being arranged so that at least some of said detectors each provide successive signals respective to paths each parallel to at least one other path for which a data signal is provided by a different detector at a different time, a selector for selecting from among said data signals different sequences of signals, each sequence of signals relating to radiation transmitted through said body along a set of parallel beam paths, and the different sequences of signals corresponding to sets of beam paths angularly distributed about said axis and means for deriving a representation of a variable characteristic, with respect to said radiation, of said slice of the body.

8. In a method of penetrating ray 3-D tomography the steps of:
  directing a divergent beam of penetrating radiation through a body to be examined from a source on one side of the body to a detector on the other side of the body;
  effecting relative angular displacement between the divergent beam of penetrating radiation and the body;
  detecting the penetrating radiation that has passed through the body at a number of angularly spaced positions within the angle subtended by the divergent beam as a function of the angular position of the divergent beam to derive sets of detected radiation data representative of a plurality of angularly spaced shadowgrams of absorption or transmission of the penetrating radiation by the body, each of said shadowgrams representing the transmission of the penetrating radiation through the body along an array of divergent paths subtended by the divergent beam, and different ones of said sets of angularly shaped shadowgraphic data corresponding to different sets of intersecting rays of penetrating radiation; and
  reordering the sets of data corresponding to absorption or transmission shadowgraphic data of divergent rays of said penetrating radiation into sets of data corresponding to absorption or transmission shadowgrams of parallel rays of said penetrating radiation.

9. The method of claim 8 including the step of, reconstructing a 3-D tomograph from said sets of parallel ray shadowgrams.

10. The method of claim 8 including the step of, transforming said sets of data corresponding to absorption or transmission shadowgrams into sets of logarithmic shadowgraphic data corresponding to the natural logarithm of said shadowgraphic data normalized to the beam intensity.

11. The method of claim 8 wherein the step of effecting relative angular displacement between the divergent beam of penetrating radiation and the body comprises effecting said relative angular displacement in a manner which is substantially free of relative lateral translation therebetween.

12. The method of claim 8 including the step of, transforming said sets of data corresponding to absorption or transmission shadowgrams into sets of logarithmic shadowgraphic data corresponding to the logarithm of said shadowgraphic data.

13. In an apparatus for obtaining a 3-D tomograph of a body to be examined:
  means for directing a divergent beam of penetrating radiation through the body to be examined from a source on one side of the body to a detector on the other side of the body;
  means for effecting relative angular displacement between the divergent beam of penetrating radiation and the body;
  means for detecting the divergent penetrating radiation that is passed through the body at a number of angularly spaced positions within the angle subtended by the divergent beam as a function of the relative angular position of the divergent beam relative to the body to derive sets of detected radiation data representative of sets of angularly spaced divergent ray shadowgrams of absorption or transmission of the divergent penetrating radiation by the body with different ones of said angularly spaced sets of the divergent ray shadowgram data corresponding to different sets of intersecting rays of divergent penetrating radiation; and
  means for reordering the sets of data corresponding to absorption or transmission shadowgrams of divergent rays of said penetrating radiation into sets of data corresponding to absorption or transmission shadowgrams of sets of parallel rays of said penetrating radiation.

14. The apparatus of claim 13 including, means for reconstructing a 3-D tomograph from said sets of parallel ray shadowgrams.

15. The apparatus of claim 13 including, means for transforming one of said sets of shadowgram data into sets of logarithmic shadowgraphic data corresponding to the natural logarithm of said parallel ray shadowgraphic data normalized to the beam intensity.

16. The apparatus of claim 13 wherein said means for effecting relative angular displacement between the divergent beam of penetrating radiation and the body includes means for effecting said relative angular displacement in a manner which is substantially free of relative lateral translation therebetween.

17. The apparatus of claim 13 including, means for transforming one of said sets of shadowgram data into sets of logarithmic shadowgraphic data corresponding to the logarithm of said parallel ray shadowgraphic data.

18. The apparatus of claim 13 including, means for transforming one of said sets of shadowgram data into sets for transforming one of said sets of shadowgram data into sets of logarithmic shadowgraphic data corresponding to the logarithm of said parallel ray shadowgraphic data normalized to the beam intensity.

* * * * *